US005504054A

United States Patent [19]
Murphy

[11] Patent Number: 5,504,054
[45] Date of Patent: Apr. 2, 1996

[54] SUPER-SPREADING, LOW-FOAM SURFACTANT FOR AGRICULTURAL SPRAY MIXTURES

[75] Inventor: Dennis S. Murphy, Leonia, N.J.

[73] Assignee: OSi Specialties, Inc., Danbury, Conn.

[21] Appl. No.: 341,587

[22] PCT Filed: Mar. 30, 1994

[86] PCT No.: PCT/US94/03523

§ 371 Date: Jan. 13, 1995

§ 102(e) Date: Jan. 13, 1995

[87] PCT Pub. No.: WO94/22311

PCT Pub. Date: Oct. 13, 1994

Related U.S. Application Data

[63] Continuation-in-part of Ser. No. 39,868, Mar. 30, 1993, abandoned.

[51] Int. Cl.$^6$ .................. A01N 25/30

[52] U.S. Cl. .................. 504/116; 71/DIG. 1; 504/206; 504/260; 504/297

[58] Field of Search .................. 504/206, 116, 504/297, 260; 71/DIG. 1

[56] References Cited

U.S. PATENT DOCUMENTS

| | | | |
|---|---|---|---|
| 3,299,112 | 1/1967 | Bailey | 260/448.2 |
| 3,562,786 | 2/1971 | Bailey et al. | 252/137 |
| 4,188,202 | 2/1980 | Gillings et al. | 71/88 |
| 4,227,911 | 10/1980 | Leonard et al. | 71/77 |
| 4,405,356 | 9/1983 | Sikorski et al. | 71/87 |
| 4,656,162 | 4/1987 | Itoh et al. | 514/63 |
| 5,017,216 | 5/1991 | Petroff et al. | 71/116 |
| 5,104,647 | 4/1992 | Policello | 514/772 |
| 5,145,978 | 9/1992 | Petroff et al. | 556/437 |

FOREIGN PATENT DOCUMENTS 991467 6/1976 Canada .

*Primary Examiner*—Brian M. Burn
*Attorney, Agent, or Firm*—Andrew S. Reiskind

[57] ABSTRACT

Methods for preparing and applying agricultural sprays without undue foaming of the spray mixture employ a superspread-promoting, low foaming trisiloxane surfactant. Agricultural spray mixtures with super-spread properties, but limited foaming, comprise (A) a superspreading, low foaming trisiloxane surfactant and (B) an agricultural chemical spray mixture comprising water, an agricultural chemical (e.g., a pesticide), and optionally an organic surfactant, antifoam agent, and an organic solvent.

16 Claims, No Drawings

SUPER-SPREADING, LOW-FOAM SURFACTANT FOR AGRICULTURAL SPRAY MIXTURES

RELATED APPLICATION

This application is a 371 of PCT/US94/03523, filed Mar. 30, 1994, which is a continuation-in-part of copending U.S. application Ser. No. 08/039,868, filed Mar. 30, 1993 (now abandoned).

FIELD OF THE INVENTION

The invention relates to agricultural, e.g. pesticide, spray mixtures. More particularly, this invention relates to a methods for preparing agricultural spray mixtures characterized by superspreading with low foaming, and for spraying them. Spray mixtures are treated with trisiloxane silicone surfactants which impart superspreading and yet exhibit low foaming, a combination of properties not previously available.

Agricultural spray mixtures can be in the form of solutions, emulsions, suspensions and dispersions, and are used in agriculture for applying agricultural chemicals which can be formed into one of the noted types of mixtures for application to plants, soil and insects. Among the typical agricultural chemicals are pesticides such as herbicides, insecticides, fungicides, growth regulators, and nutrients and micronutrients to plants and insects. They typically contain surfactants to enhance spreading when applied. When prepared with conventional surfactants, foaming often impedes mixing and creates problems even before the mixture is completely formed. Once formed, agricultural spray mixtures can foam and overflow containment vessels when transported, pumped, or subjected to motion such as vibration. Such spillage can result in loss of the agricultural spray mixture and in the contamination of surfaces by potentially toxic substances as well as losses of time and money.

Conventional trisiloxane surfactants have the ability to impart the property of superspreading to agricultural spray mixtures. By "superspreading" is meant the ability of a drop of the mixture to spread to a diameter at least 9 times as great as a doubly-distilled drop of water on a hydrophobic surface such as the leaf of a plant. However, the conventional use of trisiloxane surfactants for superspreading typically increases mixture foaming relative to the mixture in the absence of the trisiloxane surfactant.

There is a need to prevent a superspreading agricultural spray mixture from foaming or overflowing its containment vessel while not adversely affecting the mixture's spreading capability.

Silicone antifoams typically have such low surface tension values that adding such a defoamer as a separate composition to reduce surface tension doesn't work. Thus, there is a need for a new superspreading spray additive which does not create the foam problem in the first place. Likewise, there is a need for methods for preparing and utilizing a low-foam additive which still has superspread. By the term "low-foaming", it is meant that a silicone exhibits foaming of less than 50 millimeters (mm) initially and less than 15 mm after 5 minutes, using the Ross-Miles technique (ASTM method D 1173-53). Using this technique, 200 milliliters (ml) of a solution to be evaluated for foaming is allowed to fall from a height of 90 centimeters (cm). The maximum initial foam height and the foam height after 5 minutes are recorded.

The methods and compositions of the invention are based on the use of superspreading, but low-foam additives with unique molecular structures for this purpose which permit use alone or with known defoamers. It is an advantage that the low-foam, superspread-promoting additives can be used without conventional defoamers or with decreased amounts of them.

SUMMARY OF THE INVENTION

The invention provides methods for preparing and applying superspreading agricultural spray mixtures with low foaming, but without adversely affecting spreading of the mixtures when sprayed. The methods comprise adding to an agricultural spray mixture a superspreading, low-foaming surfactant comprising a trisiloxane of the following formula, hereinafter designated Formula I:

$$\begin{array}{c} CH_3 \quad CH_3 \quad CH_3 \\ | \quad\quad | \quad\quad | \\ CH_3-Si-O-Si-O-Si-CH_3 \\ | \quad\quad | \quad\quad | \\ CH_3 \quad\quad CH_3 \\ \quad\quad\quad C_nH_{2n}O[C_2H_4O]_y[C_3H_6O]_zQ \end{array}$$

wherein n has a value from about 2 to 4; y has a value of 3 to 10; z has a value from about 0 to 5; Q is selected from the group consisting of hydrogen and alkyl having 1 to 4 carbon atoms, with the provisos that when z is 0, and:
  when Q is hydrogen, y is 4 to 6;
  when Q is methyl, y is 5 to 7;
  when Q is ethyl, y is 6 to 8;
  when Q is propyl, y is 7 to 9;
  when Q is butyl, y is 8 to 10; and when z is >0, and y+z are ≦15, and y/z =1.2 to 1.8, and:
  when Q is hydrogen, y is 3 to 5, and z is 1 to 4;
  when Q is methyl, y is 4 to 7, and z is 2 to 4;
  when Q is ethyl, y is 5 to 8, and z is 3 to 5;
  when Q is propyl, y is 4 to 9, and z is 4 to 6; and
  when Q is butyl, y is 5 to 10, and z is 5 to 7.

DETAILED DESCRIPTION OF THE INVENTION

In the methods of the invention, an agricultural spray mixture is treated with the superspread-promoting, low-foaming trisiloxane surfactant set forth in Formula I (above). The superspread-promoting, low-foaming trisiloxane surfactant of Formula I can be added to a agricultural spray mixture along with the individual components during its formulation. It has been found that the order of addition of the trisiloxane surfactant to the agricultural spray mixture or its combination with the individual components of the agricultural spray mixture is not critical. It is understood that the trisiloxane surfactant can be added to a agricultural spray mixture immediately prior to spraying on plants or insects as well as its being included in the formulation of an agricultural spray mixture for spraying at a later time. By utilizing low-foaming surfactants meeting the standard described in Example 2, the final spray mixture tends to have low foaming potential relative to mixtures containing conventional organosilicone surfactants.

Superspreading, Low-foaming trisiloxane surfactants

The superspreading, low-foaming trisiloxane surfactants described by Formula I above can be prepared using procedures well known to those skilled in the art. In general, the superspreading, low-foaming trisiloxane surfactant is obtained by hydrosilylation of an alkenyl ether (e.g., vinyl, allyl, or methallyl) onto a 1,1,1,3,5,5,5-hepta-methyltrisiloxane in accordance with procedures described by W. Noll in The Chemistry and Technology of Silicones, Academic Press (New York: 1968). The superspreading, low-foaming trisiloxane of Formula I in which Q is hydrogen is formed by reacting an uncapped alkenyl polyether with a 1,1,1,3,5, 5,5-heptamethyl-trisiloxane in the presence of chloroplatinic acid at temperatures ranging from about 80° C. to 100° C. The trisiloxane of Formula I in which CI is an alkyl group having 1 to 3 carbon atoms is prepared by the reaction of an uncapped alkenyl polyether and sodium methoxide in the presence of a solvent such as toluene with heating to form the sodium salt of an allyl polyether. The salt of the allyl polyether is reacted with a 1-alkyl ($C_1$ to $C_3$) halide to form a capped alkenyl polyether which is hydrosilated with hydrotrisiloxane as set forth above.

Agricultural Spray Mixture

In general, an agricultural spray mixture contains water and an active agricultural chemical ingredient, such as a pesticide (including herbicide, insecticide, fungicide and growth regulator). Typically, at least 50 percent of the agricultural spray mixture is composed of water. Optionally, the agricultural spray mixture can contain at least one component selected from the group consisting of organic surfactant, an antifoam agent and an organic solvent. Agricultural spray mixtures are commercially available as ready-to-use products or can be prepared in a containment vessel from an agricultural chemical concentrate, water, and optionally one or more surfactants and/or antifoaming agents. It is to be understood that the low-foaming trisiloxanes employed in the present invention can be used in place of a conventional foaming trisiloxane surfactant found in any agricultural spray mixture. Conventional foaming trisiloxane surfactants as are disclosed, for example, in U.S. Pat. Nos. 3,299,112 and 4,933,002 and are available, for examples, as Silwet L-77® (OSi Specialties Inc., Danbury, Conn.) and Sylgard® 309 (Dow Corning), respectively.

The amount of the active ingredient (i.e., agricultural chemical) will be any amount effective for the intended purpose, but typically ranges from about 0.001 to about 5 percent by weight based upon the total weight of the agricultural spray mixture, e.g., from about 0.03 percent to about 0.5 percent, preferably from about 0.07 percent to about 0.25 percent based upon the total weight of the agricultural spray mixture. When the agricultural spray mixture contains an organic surfactant, the amount of the organic surfactant ranges from about 0.1 to about 5 percent by weight based upon the total weight of the agricultural spray mixture. When an antifoam agent is employed in the agricultural spray mixture it is present in an amount ranging from about 0.001 to about 0.2 percent based upon the total weight of the agricultural spray mixture. When present, the amount of the organic solvent ranges from about 0.1 to 10 percent by weight based upon the total weight of the pesticide spray mixture. The bulk or remainder of the agricultural spray mixture is comprised of water.

Illustrative pesticides which can be employed as the active ingredient in the agricultural spray mixture of the present invention include those from the groups consisting of growth regulators, photosynthesis inhibitors, mitotic disruptors, lipid biosynthesis inhibitors, cell wall inhibitors, and cell membrane disruptors.

Growth regulators:
Phenoxy Acetic Acids, such as 2-4-D [(2,4-Dichlorophenoxy)acetic acid]
Phenoxy Propionic Acids, such as Dichlorprop [(RS)-2-(2, 4-dichlorophenoxy)propionic acid] Mecoprop [(RS)-2-(4-chloro-o-tolyloxy)propionic acid]
Phenoxy Butyric Acids, such as 2,4-DB [4-(2,4-Dichlorophenoxy)butyric acid]
Benzoic Acids, such as Dicamba [3.6-dichloro-o-anisic acid]
Other growth regulators, such as Fluoroxypyr [4-amino-3, 5-dichloro-6-fluoro-2-pyridloxyacetic acid] Picloram [4-amino-2,3,5-trichloro-2-carboxylic acid] Triclopyr [3,6-dichloropyridine-2-carboxylic acid] Copyralid [3,6-dichloropyridine-2-carboxylic acid] Gibberellic acid (3S, 3aR, 4S, 4aS, 7S, 9aR, 9bR, 12S) -dihydroxy-3-methyl-6-methylene-2-oxoperhydro-4a, 7-methano-9b,3-propenoazuleno[1,2-b]furan-4-carboxylic acid Photosynthesis inhibitors:
Traizines and s-Triazines such as Hexazinone [3-cyclohexyl-6-dimethylamino-1-methyl-1,3,5 -triazine-2,4(1H, 3H)-dione] Metribuzin [4-amino-6-tert-butyl-3-methylthio-1,2-3-triazine-5(4H )-one ] Atrazine [6-chloro-$N^2$-ethyl-$N^4$-isopropy]1-1,3,5-triazine-2,4-diamine] Simazine [6-chloro-$N^2$,$N^4$-diethyl-1,3,5-triazine-2,4-diamine] Cyasnazine 2-[[4-chloro-6-(ethylamino)-1,3,5-triazin-2-yl]-amino] -2-methylpropanenitrile Prometon[$N^2$, $N^2$4-di-isopropyl-6-methoxy-1,3,5-triazine-2,4-diamine] Ametryn [$N^2$-ethyl-$N^2$-isopropyl-6-methylthio-1,3,5 triazine-2,4-diamine]

Substituted ureas, such as Diuron [3-(3,4-dichlorophenyl)-1,1-dimethylurea(I)] Fluometuron [1,1-dimethyl-3-(a,a,a, -trifluoro-m-tolyl)urea(I)] Linuron [3-(3,4-dichlerophenyl)-1-methoxy-1-methylurea(I)] Tebuthiuron [1-(5-tert-butyl, 1,3,4-thiadiazol-1-yl)-1,3-dimethylurea(I)]

Uracils, such as Bromacil [5-bromo-3-sec-butyl-6-methylureacil(I)] Terbacil [3-tert-butyl-5-chloro-6-methyluracil(I)]

Other photsynthesis inhibitors, such as Bentazon [3-isopropyl-1H-2,1,3-benzothiadazin-4(3H)-one 2,2-dioxide(I)] Desmedipham [ethyl 3'-phenylcarbamoyloxycarbanilate; ethyl 3-phenylcarbamoyloxypenylcarbamate; 3-ethoxycarbonylaminophenyl phenylcarbamate.] Methazole [2-(3,4-dichlorophenyl)-4-methyl-1,2,4- oxadiazolidine-3,5-dione(I)] Phenmedipham [methyl 3-(3methylcarbaniloyloxy) carbanilate; 3'-methoxycarbonylaminophenyl 3'-methylcarbanilate.] Propanil [3',4'-dichloropropionanilide(I)] Pyridate [6-chloro-3-phenylpyridazine-4-yl S-octyl thiocarbonate]

Pigment Inhibitors: such as

Amitrole, [1H-1,2,4-triazol-3-ylamine; 3-amino-1H-1,2,4-triazole] Clomazone [2-(2-chlorobenzyl)-4,4-dimethyl-1, 2-oxazolidin-3-one; 2-(2-chlorobenzyl)-4,4-dimethyl-isoxzazolidin-3-one] Fluridone [1-methyl-3-phenyl-5-(a, a,a-trifluoro-m-tolyl)-4-pyridone] Norflurazone [4-chloro-5-methylamino-2-(a,a,a-trifluoro-m-tolyl)pyridazine-3(2H-one]

Mitotic disruptors:

Dinitroanilines, such as Isopropalin [4-isopropyl-2,6-dinitro-N, N-dipropylaniline] Oryzalin [3,5-dinitro-N,N-dipropylsulfanilamine(I)] Pendimethalin [N-(1-ethylpropyl)-2,6-dinitro-3,4-xylidine] Prodiamine [5-dipropylamino-1,a,a-trifluoro-4-6-dintro-o-toluidine; 2,6-dinitro-$N^1$,$N^1$-dipropyl-4-trifluormethyl-m-phenylenediamine] Trifluralin [a,a,a-trifluoro-2,6-dinitro-N, N-dipropyl-p-toluidine(I)]

Inhibitors of amino acid synthesis, such as Glyphosate [N-(phosphonomethyl)glycine(I)]

Sulfonylureas, such as Bensulfuron [a-(4,6-dimethoxypyrimidin-2-ylcarbamolysulfamoyl)-o-toluic acid] Chlorimuron [2-(4-chloro-6-methoxypyrimidin-2-ylcarbamoylsulfamoyl)benzoic acid] Chlorsulfuron [1-(2-chlorophylsulfonyl)-3-(4-methoxy-6-methyl-1,3,5-triazin-2-yl)urea] Metsulfuron [2-(4-methoxy-5-methyl- 1,3,5-triazin-2-ylcarbamoylsulfamoyl)benzoic acid] Nicosulfuron [2-(4,6-dimethoxypyrimidin-2-ylcarbamoylsulfamoyl)-N,N-dimethyl-nicotinamide; 1-(4,6-dimethoxy-pyrimidin-yl)-3-(3-dimethylcarbamoyl-2-pyridylsulfonyl)urea] Primisulfuron [2-[4-6-bis-(difluoromethoxy)pyrimidin-2-ylcarbamoylsulfamoyl] benzoic acid] Sulfometuron [2,(4,6-dimethylpyrimidin-2-ylcarbamoylsulfamoyl)benzoic acid; 2-[3-(4,6-dimethylpyrimidin-2yl)-ureidosulfonyl]benzoic acid] Thifensulfuron [3-(4-methoxy-5-methyl-1,3,5-triazine-2-ylcarbamoylsulfamoyl)thiophen-2-carboxylic acid] Trisulfuron [1-[2-(2-chloroethoxy)phenylsulfonyl]-3(4-methoxy-6-methyl-1,3,5-triazin-2yl)urea] Tribenuron [2-[4-methoxy-6-methyl-1,3,5-triazin-2-yl(methyl)carbamoylsulfamoyl]benzoic acid]

Imidazolines, such as Imazamethabenz [a reaction product comprising (+)-6-(4-isopropyl-4-methyl-5-oxo-2-imadazoli n-2-yl)-m-toluic acid (i) and (+)-2-(4-isopropyl-4-methyl-5-oxo-2-imidazolin-2-yl)-p-toluic acid (ii)] Imazapyr [2-(4-isopropyl-4-methyl-5-oxo-2-imidazolin-2-yl)nicotinic acid] Imazaquin [(RS)-2-(4-isopropyl-4-methyl-5-oxo-2 -imadazolin-2-yl)quinoline-3-carboxylic acid] Imazethapyr [(RS)-5-ethyl-2-(4-isopropyl-4-methyl-5 -oxo-2-imidazolin-2-yl)nicotinic acid]

Inhibitors of lipid biosynthesis, such as Clethodim [(+)-2-[(E)-3-chloroallyloxyimino]propyl]5[2-(ethylthio)propyl]-3-hydroxycyclohex-3-enone] Diclofop-methyl [(RS)-2-[4-2,4-dichlorophenoxy)phenoxy]propionic acid] Fenoxaprop-ethyl [+-2-[4-(6-chloro-1,3-benzoxazol-2-yloxy)phenoxy]propionic acid; (+)-2-[4-(5-chlorobenzoxazol-2-yloxy)phenoxy]propionic acid] Fluazifop-P-butyl [(R)-2-[4-(5-trifiuromethyl-2-pyridlyoxy)phenoxy]propionic acid] Haloxyfop-methyl [(RS)-2-[4-(3-chloro-5 -trifluoromethyl-2-pyridyloxy)phenoxy]propionic acid] Quizalofop [(RS)-2[4-(6-chloroquinoxalin-2-yloxy)phenoxy]propionic acid] Sethoxydim [(+)-(EZ)-2-(1-ethoxyiminobutyl)-5-[2 -(ethylthio)propyl]-3-hydroxycyclohex-2-enone]

Cell wall inhibitors, such as Dichlobenil [2,6-dichlorobenzonitrile(I)] Isoxaben [N-[3-(1-ethyl-1-methylpropyl)-1, 2-oxazol-5 -yl]-2,6-dimethoxybenzamide; N-[3-(1-ethyl-1-methylpropyl)isoxazol-5-yl]-2,6-dimethoxybenzamide]

Cell membrane disruptors:

Bipyridylium compounds such as Diquat [9,10-dihydro-8a-diazoniaphenanthrene; 6-7-dihydrodipyridol[1,2-a:2',1'-c]pyrazine-5,8-di-ium; 1,1'-ethylene-2,2'-bipyridyldiylium] Paraquat [1,1'-dimethyl-4,4'bipyridinium(I)]

Diphenylethers, such as Acifluorfen [5-(2-chloro-a,a,a-trifluro-p-tolyoxy)-2-nitrobenzoic acid]

Preferred pesticides include, for example, glyphosate available as Roundup® from Monsanto; gibberellic acid available as Pro-Gibb® from Abbott Laboratories; and triclopyr available as Garlon® from Dow Elanco.

Organic surfactants that can be employed in the invention are defined as surfactants which have a hydrocarbon based group as the hydrophobic moiety (i.e., he water insoluble component of the surfactant such as, for example an alkyl group having 7 to 12 carbon atoms). Organic surfactants contained in an agricultural spray mixture are readily commercially available. For example, they can be obtained from McCutcheon's, *Emulsifiers & Detergents*, North American Edition (MC Publishing Co., Glen Rock, N.J., 1992). Illustrative organic surfactants can include, for example, carboxylic acid salts such as Dresinate® TX, Hercules Inc. (Wilmington, Del.); linear alkyl benzenesulfonates such as BioSoft® LAS-405, Stepan Co. (Northfield, Ill.); ligninsulfonates such as Lignosite® 231, Georgia Pacific Corp. (Atlanta, Ga.); a-olefin sulfonates such as Calsofi® AOS-40, Pilot Chemicals Co. (Santa Fe Springs, Calif.); sulfosuccinate esters such as Aerosol® OT, American Cyanamid (Wayne, N.J.); sulfates of linear primary alcohols such as Polystep® B-3, Stepan Co. (Northfield, Ill.); sulfated polyoxyethylenated straight-chain alcohols such as Neodol® 25-3A, Shell Chemical Co. (Houston, Tex.); quaternary ammonium salts such as Emcol® CC-9, Witco Corp. (New York, N.Y.); amine oxides such as Admox® 1214, Ethyl Corp. (Baton Rouge, La.); polyoxyethylenated alkylphenols such as DeSonic® N, DeSoto Inc. (Fort Worth, Tex.); polyoxyethylenated straight-chain alcohols such as Brij® 30, ICI Americas, Inc. (Wilmington, Del.); polyoxyethylenated polyoxypropylene glycols such as Pluronic® L63, BASF Corp. (Parsippany, N.J.); N-alkylpyrrolidones such as Surfadone® LP-100, GAF Chemicas Corp. (Wayne, N.J.); N-alkylbetaines such as Mirataine® BB, Miranol Inc. (Dayton, N.J.). Preferably the organic surfactant is selected from the group consisting of sulfated polyoxyethylenated straight chain alcohol, polyoxyethylenated straight chain alcohol, and a sulfate of a linear primary alcohol. The preferred organic surfactants preferably have 7 to 12 carbon atoms in the hydrophobic moiety of the organic surfactant.

Antifoam agents which can be used in an agricultural spray mixture are also readily commercially available. Typically, these antifoam agents are silica-filled silicone emulsions. Illustrative antifoam agents can include, for example, SAG® MARK X and SAG® 10, available from Union Carbide Chemicals and Plastics Company Inc. (Danbury, Conn.); GE AF-9020®, available from General Electric Co. (Waterford, N.Y.); FOAM BUSTER® (Helena Chemical Company; Memphis, Tenn.); and FIGHTER F®, available from Loveland Industries, Inc. (Loveland, Colo.).

Optionally, an organic solvent can be employed in the agricultural spray mixture. When employed, the solvent can include a lower molecular weight alcohol having 1 to 5 carbon atoms such as, for example, methanol, ethanol, n-propanol, isopropanol, n-butanol, t-butanol, and n-amyl alcohol. Ketones having 1 to 6 carbon atoms such as, for example, acetone and methyl-butyl ketone can also be used as a solvent.

The following specific examples are presented to further illustrate and explain certain aspects of the present invention. However, the examples are set forth for illustration only, and are not to be construed as limiting on the present invention. In the following examples, all percentages and parts are by weight unless otherwise specified.

EXAMPLE 1

The trisiloxane surfactants employed in the Examples are set forth below in Table 1.

TABLE 1

Trisiloxane Surfactants

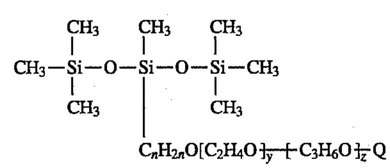

| TRISILOXANE | y | z | Q |
|---|---|---|---|
| SILICONE 1 | 8 | 0 | $CH_2CH_2CH_3$ |

TABLE 1-continued

Trisiloxane Surfactants $$CH_3-\underset{\underset{CH_3}{|}}{\overset{\overset{CH_3}{|}}{Si}}-O-\underset{\underset{C_nH_{2n}O[C_2H_4O]_{\overline{y}}[C_3H_6O]_{\overline{z}}Q}{|}}{\overset{\overset{CH_3}{|}}{Si}}-O-\underset{\underset{CH_3}{|}}{\overset{\overset{CH_3}{|}}{Si}}-CH_3$$

| TRISILOXANE | y | z | Q |
|---|---|---|---|
| SILICONE 2 | 6 | 0 | $CH_3$ |
| SILICONE A | 8 | 0 | $CH_3$ |
| SILICONE B | 8 | 0 | $CH_2(CH_2)_3CS_3$ |
| SILICONE C | 3.5 | 0 | H |

In each structure above, the amount of ($C_2H_4O$) represents an average. Silicone A is sold under the trademark SILWET L-77® by OSi Specialties Inc.

Spreading Test

Superspreading of trisiloxane surfactants makes them of use for agricultural applications. A low-foaming surfactant should possess the ability to superspread. Substrates on which spreading was evaluated were Parafilm M (paraffin wax film) and polyster film (IR 1174 from 3M).

Spreading tests on Parafilm M were performed as follows. A 10-microliter drop of the mixture was placed, using an automatic micropipetter, on a piece of Parafilm M stretched across the mouth of a jar on a level table top. At the point of maximum spreading, or after 5 minutes, the largest and smallest diametric dimensions of the spread drop were measured. Each material was tested at least twice and the measurements were averaged.

Spreading tests on polyester film (IR 1174) were performed as follows. A 10-microliter drop of the mixture was placed, using an automatic micropipetter, on a piece of polyester film. At the point of maximum spreading, or after 5 minutes, the largest and smallest diametric dimensions of the spread drop were measured. Each material was tested at least twice and the measurements were averaged.

The spreading factor on each surface was calculated as the ratio of the average diameter of a drop of the surfactant solution to that of a doubly distilled water drop. For purposes of this calculation the doubly distilled water drop was designated as having a value of 1. Superspreading was present when a spreading factor was greater than 9 on each surface. Results of the spreading tests are shown in Table 2.

TABLE 2

Spreading Factors for 0.1% Trisiloxane Surfactant Mixtures

| Run | Trisiloxane | On Parafilm | On Polyester Film |
|---|---|---|---|
| 1 | SILICONE 1 | 11.9 | 12.6 |
| 2 | SILICONE 2 | 9.7 | 13.0 |
| A | SILICONE A | 9.4 | 11.0 |
| B | SILICONE B | 2.3 | 6.0 |
| C | SILICONE C | 4.0 | 3.7 |

It can be seen that Silicones 1 and 2, in accordance with the present invention, superspread. In addition, Silicone A also superspreads. Silicones B and C did not superspread, and, hence were not evaluated further for foaming.

EXAMPLE 2

Surfactant Foaming Requirements

Silicones 1,2 and A which superspread in Example 1 were tested for foaming. Foaming tests were performed using the Ross-Miles technique (ASTM method D 1173-53). Using this technique, 200 milliliters (ml) of a solution to be evaluated for foaming is allowed to fall from a height or 90 centimeters (cm). The maximum initial foam height and the foam height after 5 minutes were recorded. For this evaluation, a silicone should exhibit foaming of less than 50 millimeters (mm) initially and less than 15 mm after 5 minutes. Results are shown in Table 3, to be considered low foaming.

TABLE 3

Ross-Miles Foaming Using 0.1% Surfactant Mixtures

| Run | Trisiloxane | Initial Foam Height (mm) | 5 minute Foam Height (mm) |
|---|---|---|---|
| 3 | SILICONE 1 | 18 | 9 |
| 4 | SILICONE 2 | 39 | 9 |
| D | SILICONE A | 90 | 85 |

From Table 3 it is seen that SILICONE 1 and SILICONE 2 have foam heights less than 50 mm initially and less than 15 mm after 5 minutes. In contrast, the comparative Silicone A showed foaming greater than 50 mm initially and greater than 15 mm after 5 minutes.

EXAMPLE 3

Use of Low-foaming Siloxane in an Agricultural Spray Mixture

SILICONE 1 and SILICONE A were each separately blended into a conventional pesticide spray solution (RoundupRun® Ready-To-Use from Monsanto Co., St. Louis, Mo.). SILICONE A is a conventional trisiloxane surfactant such as those taught in U.S. Pat. No. 3,299,112 and commercially available as Silwet L-77®. To 20 milliliters of an agricultural spray mixture, containing 0.20 milliliters of the pesticide glyphosate, was added 0.04 grams to make a 0.2% trisiloxane surfactant in the agricultural spray solution in a 100-ml graduated cylinder which was then stoppered. The stoppered cylinder was shaken vigorously by hand 30 times. All the experiments were performed by the same operator. The foam volume was recorded as a function of time and these results are set forth in Table 4.

TABLE 4

Foaming Properties of Agricultural Spray Mixture/ Trisiloxane Surfactant

| Run | Trisiloxane | Time (Min.) | Foam Volume |
|---|---|---|---|
| 5 | SILICONE 1 | 0 | 60 |
|   |   | 5 | 42 |
|   |   | 10 | 17 |
| E | SILICONE A | 0 | 65 |
|   |   | 5 | 50 |
|   |   | 10 | 48 |

From Table 4, it can be seen that Agricultural Spray Mixture/Silicone 1 (Run 5) produced less foam than Agricultural Spray Mixture/Silicone A (Run E).

EXAMPLE 4

Effect of Antifoam in an Agricultural Spray Mixture

A commercially available, conventional antifoam (SAG® MARK X from Union Carbide Chemicals and Plastics Company Inc., Danbury, Conn.) 0.002 grams, to make 0.01% of antifoam in the agricultural spray mixture was employed and evaluated with both Silicone 1 and Silicone A, as done in Example 3. Results are shown in Table 5.

TABLE 5

Foaming Properties of Agricultural Spray Mixture/Antifoam/Trisiloxane Surfactant

| Run | Trisiloxane | Time (Min.) | Foam Volume (ml) |
|---|---|---|---|
| 6 | SILICONE 1 | 0 | 32 |
|   |   | 1 | 5 |
|   |   | 5 | 2 |
|   |   | 10 | 2 |
| F | SILICONE A | 0 | 63 |
|   |   | 1 | 48 |
|   |   | 5 | 40 |
|   |   | 10 | 23 |

From Table 5, it can be seen that the agricultural spray mixture containing the superspread-promoting, low-foaming trisiloxane surfactant (Silicone 1) is more easily defoamed than the mixture incorporating Silicone A whose chemical structure is different from that of the low-foaming trisiloxane surfactant of the present invention.

EXAMPLE 5

Use of Superspreading, Low-foaming Trisiloxane with Other Agricultural Chemicals This Example demonstrated that the low-foaming trisiloxane can be employed with agricultural chemicals other than that contained in the pesticide Roundup® (i.e., glyphosate). Gibberellic acid (as Pro-Gibb® from Abbott Laboratories, Chicago, Ill.) and triclopyr (from a 44.4% active concentrate of Garlon® 3A from Dow-Elanco, Indianapolis, Ind.), were employed. The amount of agricultural chemical in each solution was typical of use levels in the field. The same experimental technique employed in Example 3 was used. Results are shown in Tables 6 and 7.

TABLE 6

Foaming Properties of Spray Mixtures Containing 40 ppm of Gibberellic Acid and 0.2% of a Trisiloxane Surfactant

| Run | Surfactant | Time (Min.) | Foam Volume (ml) |
|---|---|---|---|
| 6 | SILICONE 1 | 0 | 33 |
|   |   | 1 | 9 |
|   |   | 5 | 6 |
|   |   | 10 | 6 |
| G | SILICONE A | 0 | 40 |
|   |   | 1 | 20 |
|   |   | 5 | 16 |
|   |   | 10 | 13 |

TABLE 7

Foaming Properties of Spray Mixtures Containing 1.6% Triclopyr and 0.2% of a Trisiloxane Surfactant

| Run | Surfactant | Time (Min.) | Foam Volume (ml) |
|---|---|---|---|
| 8 | SILICONE 1 | 0 | 7 |
|   |   | 1 | 7 |
|   |   | 5 | 6 |
|   |   | 10 | 6 |
| H | SILICONE A | 0 | 50 |
|   |   | 1 | 40 |
|   |   | 5 | 30 |
|   |   | 10 | 27 |

From the results, it can be seen that the Agricultural Spray Mixtures/Silicone 1 (Runs 7 and 8) produced less foam than Agricultural Spray Mixtures/Silicone A (Runs G and H).

The above description is for the purpose of teaching the person of ordinary skill in the art how to practice the present invention, and it is not intended to detail all of those obvious modifications and variations of it which will become apparent to the skilled worker upon reading the description. It is intended, however, that all such obvious modifications and variations be included within the scope of the present invention which is defined by the following claims.

For conciseness, several conventions have been employed with regard to listings of chemicals and ranges. The listings of chemical entities throughout this description are meant to be representative and are not intended to exclude equivalent materials, precursors or active species. Also, each of the ranges is intended to include, specifically, each integer, in the case of numerical ranges, and each species, in the case of chemical formulae, which is encompassed within the range. The claims are meant to cover the claimed components and steps in any sequence which is effective to meet the objectives there intended, unless the context specifically indicates the contrary.

What is claimed is:

1. A superspreading, low-foam agricultural spray mixture comprising (A) a superspreading, low-foaming surfactant comprising a trisiloxane having the formula:

$$\begin{array}{ccc} CH_3 & CH_3 & CH_3 \\ | & | & | \\ CH_3-Si-O-Si-O-Si-CH_3 \\ | & | & | \\ CH_3 & & CH_3 \\ & C_nH_{2n}O[C_2H_4O]_y[C_3H_6O]_zQ \end{array}$$

wherein n has a value from about 2 to 4; y has a value of 3 to 10; z has a value from about 0 to 5; Q is selected from the group consisting of hydrogen and alkyl having 1 to 4 carbon atoms, with the provisos that
when z is 0, and:
  when Q is methyl, y is 5 to 6;
  when Q is ethyl, y is 6 to 8;
  when Q is propyl, y is 7 to 9;
  when Q is butyl, y is 8 to 10; and,
when z is >0, and y+z are ≦15, and y/z=1.2 to 1.8, and:
  when Q is hydrogen, y is 3 to 5, and z is 1 to 4;
  when Q is methyl, y is 4 to 7, and z is 2 to 4;
  when Q is ethyl, y is 5 to 8, and z is 3 to 5;
  when Q is propyl, y is 4 to 9, and z is 4 to 6;
  when Q is butyl, y is 5 to 10, and z is 5 to 7; and (B) an agricultural spray mixture comprising water, and an agricultural chemical.

2. The composition of claim 1 wherein, in the trisiloxane surfactant, n is 3;

z is 0;

and when Q is methyl, y is 6; ethyl, y is 7; and when Q is propyl, y is 8.

3. The composition of claim 1 wherein the agricultural chemical is a pesticide selected from the group consisting if gibberellic acid, triclopyr and glyphosate.

4. The composition of claim 1 wherein the agricultural spray mixture additionally comprises at least one component selected from the group consisting of an organic surfactant, an antifoam agent, and an organic solvent.

5. The composition of claim 4 wherein the organic surfactant has a hydrocarbon group having 7 to 12 carbon atoms as a hydrophobic moiety and is selected from the group consisting of (i) a carboxylic acid salt;

(ii) a linear alkyl benzenesulfonate (iii) a ligninsulfonate;

(iv) an α-olefin sulfonate;
(v) a sulfosuccinate ester;
(vi) a sulfate of a linear primary alcohol;
(vii) a sulfated polyoxyethylenated straight-chain alcohol;

(viii) a quaternary/ammonium salt (ix) an amine oxide;

(x) a polyoxyethylenated alkylphenol;
(xi) a polyoxyethylenated straight-chain alcohol;
(xii) a polyoxyethylenated polyoxypropylene glycol;
(xiii) an N-alkylpyrrolidone; the antifoam agent is a silica-filled silicone emulsion; and the organic solvent is selected from the group consisting of isopropanol, ethanol and acetone.

6. A method for preparing a superspreading agricultural spray without creating undue amounts of foam, which method comprises adding to a sprayable agricultural mixture, a superspreading, low-foaming surfactant comprising a trisiloxane having the formula:

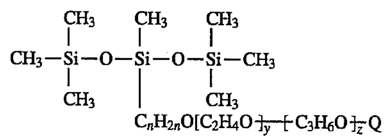

wherein n has a value from about 2 to 4; y has a value of 3 to 10; z has a value from about 0 to 5; Q is selected from the group consisting of hydrogen and alkyl having 1 to 4 carbon atoms, with the provisos that when z is 0, and:

when Q is methyl, y is 5 to 6;

when Q is ethyl, y is 6 to 8;

when Q is propyl, y is 7 to 9; and when Q is butyl, y is 8 to 10; and, when z is >0, and y+z are ≦15, and y/z=1.2 to 1.8, and:

when Q is hydrogen, y is 3 to 5, and z is 1 to 4;

when Q is methyl, y is 4 to 7, and z is 2 to 4;

when Q is ethyl, y is 5 to 8, and z is 3 to 5;

when Q is propyl, y is 4 to 9, and z is 4 to 6;

when Q is butyl, y is 5 to 10, and z is 5 to 7.

7. The method of claim 6, where n is 3 and z is 0 and when Q is methyl, y is 6; and when Q is ethyl, y is 7 and when Q is propyl, y is 8.

8. The method of claim 6 wherein the agricultural spray mixture comprises an agricultural chemical and water.

9. The method of claim 8 wherein the agricultural chemical is a pesticide selected from the group consisting of gibberellic acid, triclopyr, and glyphosate.

10. The method of claim 8 wherein the agricultural spray mixture additionally comprises at least one component selected from the group consisting of an organic surfactant, antifoam agent, and an organic solvent.

11. The method of claim 10 wherein the organic surfactant has a hydrocarbon group having 7 to 12 carbon atoms as a hydrophobic moiety and is selected from the group consisting of:

(i) a carboxylic acid salt;

(ii) a linear alkyl benzenesulfonate (iii) a ligninsulfonate;

(iv) an α-olefin sulfonate;

(v) a sulfosuccinate ester;

(vi) a sulfate of a linear primary alcohol;

(vii) a sulfated polyoxyethylenated straight-chain alcohol;

(viii) a quaternary ammonium salt (ix) an amine oxide;

(x) a polyoxyethylenated alkylphenol;

(xi) a polyoxyethylenated straight-chain alcohol;

(xii) a polyoxyethylenated polyoxypropylene glycol; and (xiii) an N-alkylpyrrolidone.

12. The method according to claim 10 wherein the antifoam agent is a silica-filled silicone emulsion.

13. The method of claim 10 wherein the organic solvent is selected from the group consisting of isopropanol, ethanol, and acetone.

14. A method of applying a agricultural spray comprising:

preparing an agricultural spray mixture as set out in claim 6; and spraying said mixture onto plants.

15. A superspeading, low-foam agricultural spray mixture consisting essentially of:

(A) a superspreading, low foaming surfactant of the general structure of $(CH_3)_3Si—O—Si(CH_3)(R)—O—Si(CH_3)_3$, where R is $C_nH_{2n}O[C_2H_4O]_y[C_3H_6O]_z—Q$ wherein n has the value from about 2 to 4; y has a value of 3 to 10; z has a value from about 0 to 5; Q is selected from the group consisting of hydrogen and alkyl having 1 to 4 carbon atoms, with the provisos that:

when z is 0, and:

when Q is hydrogen, y is 4 to 5;

when Q is methyl, y is 5 to 6;

when Q is ethyl, y is 6 to 8;

when Q is propyl, y is 7 to 9;

when Q is butyl, y is 8 to 10; and, when z is >0, and y+z are ≦15, and y/z is 1.2 to 1.8, and:

when Q is hydrogen, y is 3 to 5, and z is 1 to 4;

when Q is methyl, y is 4 to 7, and z is 2 to 4;

when Q is ethyl, y is 5 to 8, and z is 3 to 5;

when Q is propyl, y is 4 to 9, and z is 4 to 6;

when Q is butyl, y is 5 to 10, and z is 5 to 7; and (B) water; and (C) an agricultural chemical.

16. The composition of claim 15 wherein the agricultural spray mixture additionally comprises at least one component selected from the group consisting of an organic surfactant, an antifoam agent and an organic solvent.

* * * * *